United States Patent [19]

Walker et al.

[11] Patent Number: 5,123,417
[45] Date of Patent: Jun. 23, 1992

[54] APPARATUS AND METHOD FOR DISPLAYING ULTRASONIC DATA

[75] Inventors: Jack Walker, Sunnyvale; Quang Ton; John Geis, both of San Jose; John Schultz, Santa Clara; Richard Lee, San Jose, all of Calif.

[73] Assignee: Diasonics, Inc., Milpitas, Calif.

[21] Appl. No.: 555,985

[22] Filed: Jul. 19, 1990

[51] Int. Cl.⁵ .................................................. A61B 8/06
[52] U.S. Cl. .................................. 128/661.09; 358/82
[58] Field of Search ................................. 358/81, 82; 128/660.04–660.05, 661.07–661.10; 73/861.25

[56] References Cited

PUBLICATIONS

"Colour Flow Mapping Data Analysis . . . Linking the Vingmed CFM With the Apple Mac II," Vingmed Sound, Interspec, 110 West Butler Avenue, Ambler, PA 19002-5795 (undated).

*Primary Examiner*—Francis Jaworski
*Attorney, Agent, or Firm*—Blakely, Sokoloff, Taylor & Zafman

[57] ABSTRACT

The method of the present invention comprises displaying an image comprising reflected pulsed doppler signals in real time produced by reflecting a reference pulsed doppler signal, each reflected signal displayed in a color defined by a polar coordinate plot, wherein the polar coordinate plot comprises an origin representing reflected signals of the reference pulsed doppler signal having zero amplitude and zero frequency. The polar coordinate plot further comprises an axis representing reflected signals of the reference pulsed doppler signal having zero frequency, a radius with respect to the origin representing amplitude information of reflected signals of the reference pulsed doppler signal, an angle with respect to the axis representing the frequency of reflected signals of the reference pulsed doppler signal, and a vector displaced 180 degrees from the axis, the vector representing a Nyquist limit of the reference pulsed doppler signal. The colors on the plot in a positive direction at a maximum amplitude for a first frequency towards a point representing maximum amplitude for a second frequency range from a first color to a second color, colors on the plot in a negative direction at a maximum amplitude for a third frequency towards a point for a maximum amplitude for a fourth frequency range from a third color to a fourth color, and the colors for each frequency on the plot range from the color at a maximum amplitude for each frequency to a fifth color at the origin.

10 Claims, 12 Drawing Sheets

FIG__1
(PRIOR ART)

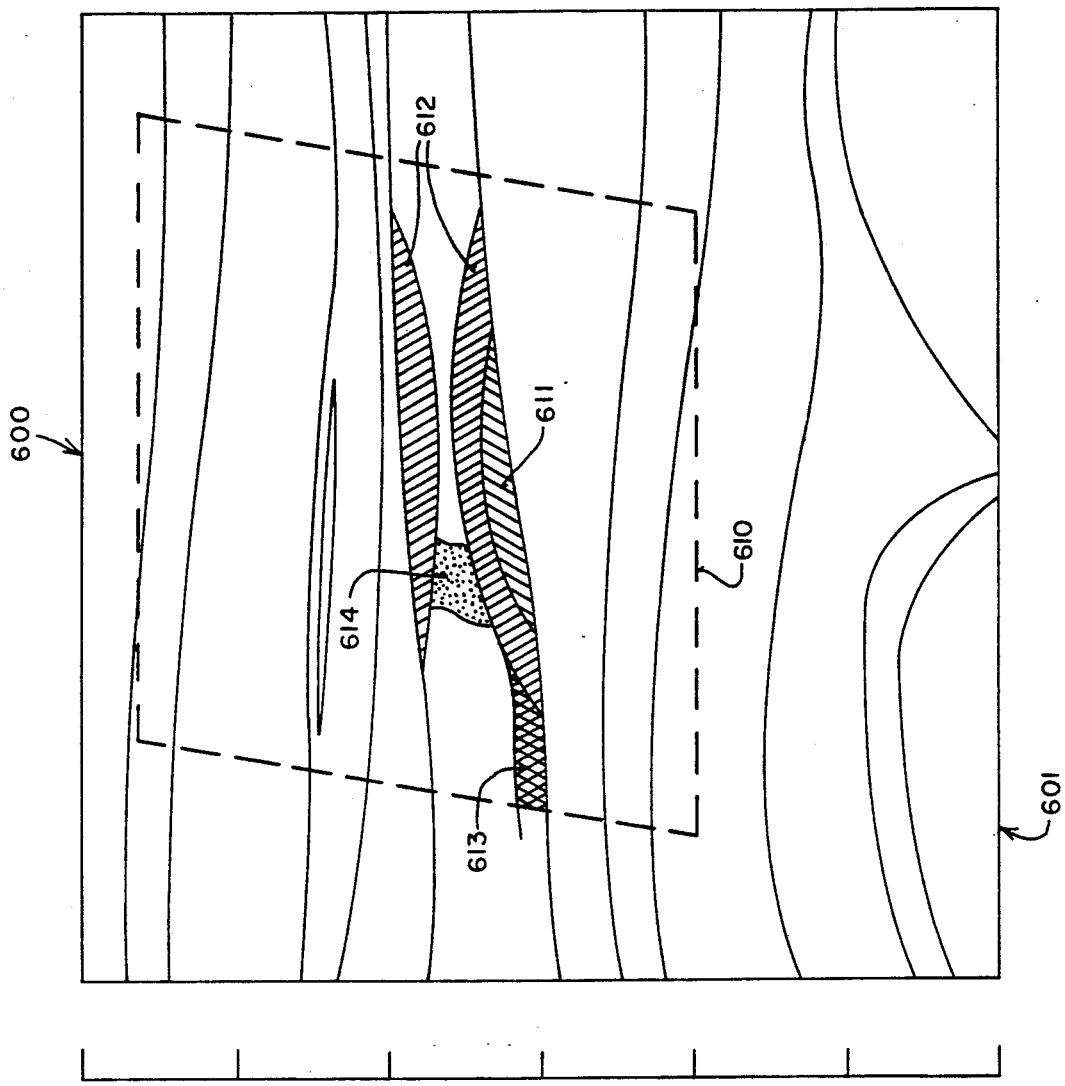
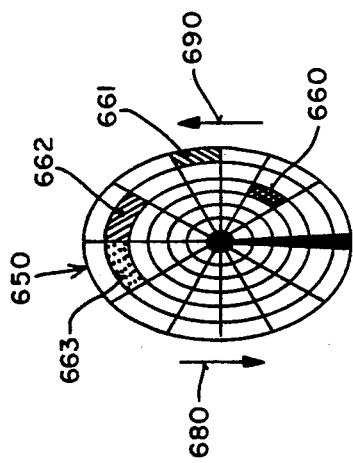
FIG_3
RED BLUE
PRF = 3497 HZ
FD = NORM
TF = ∅

FIG_4A
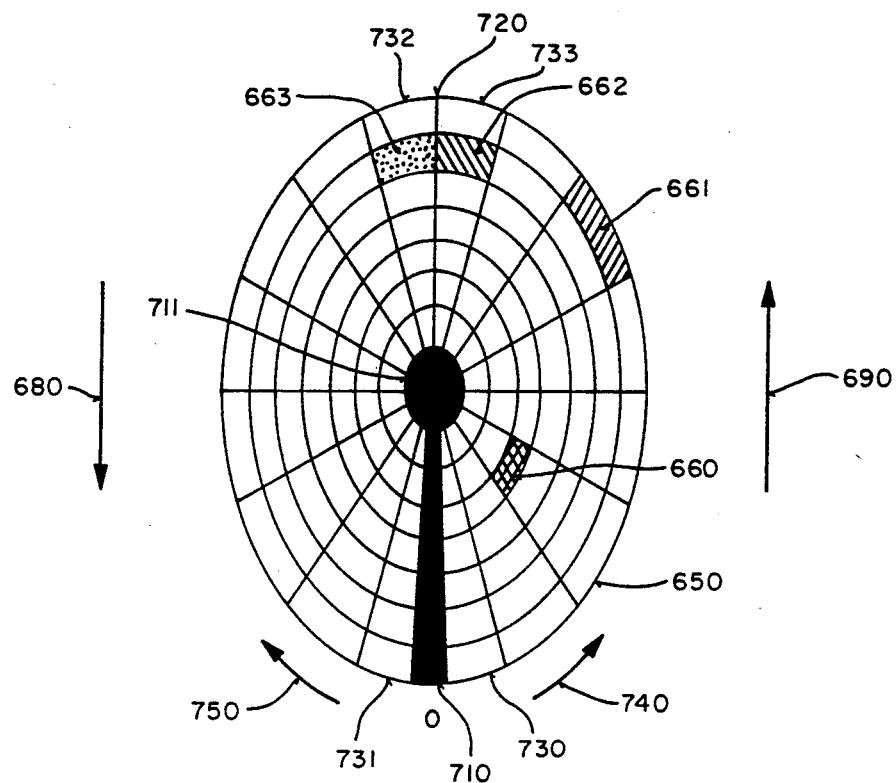
FIG_4B (PRIOR ART)
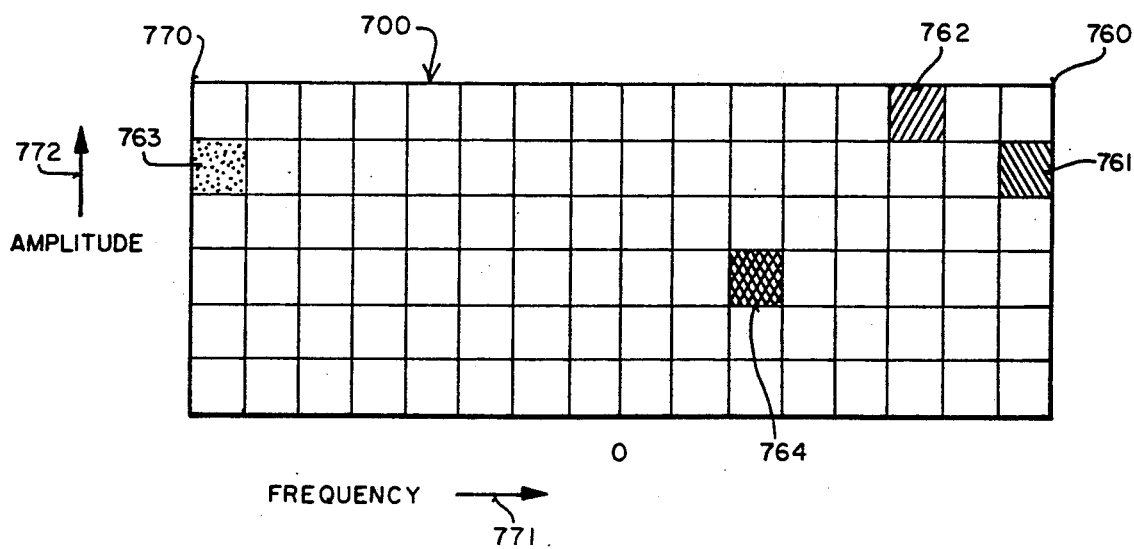
AMPLITUDE
FREQUENCY →
771

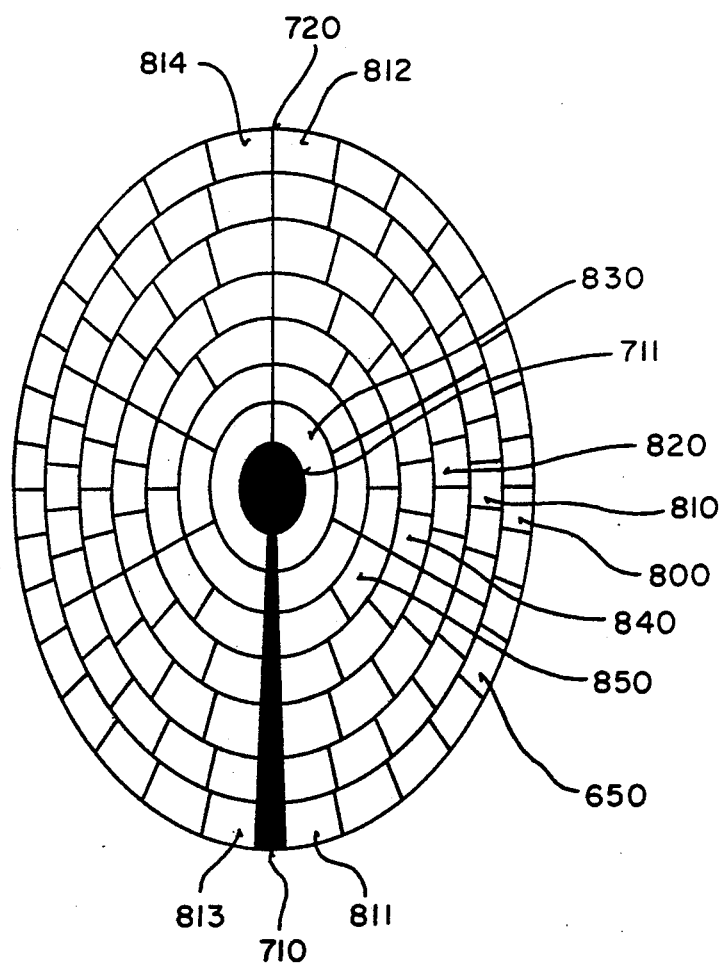
FIG_5

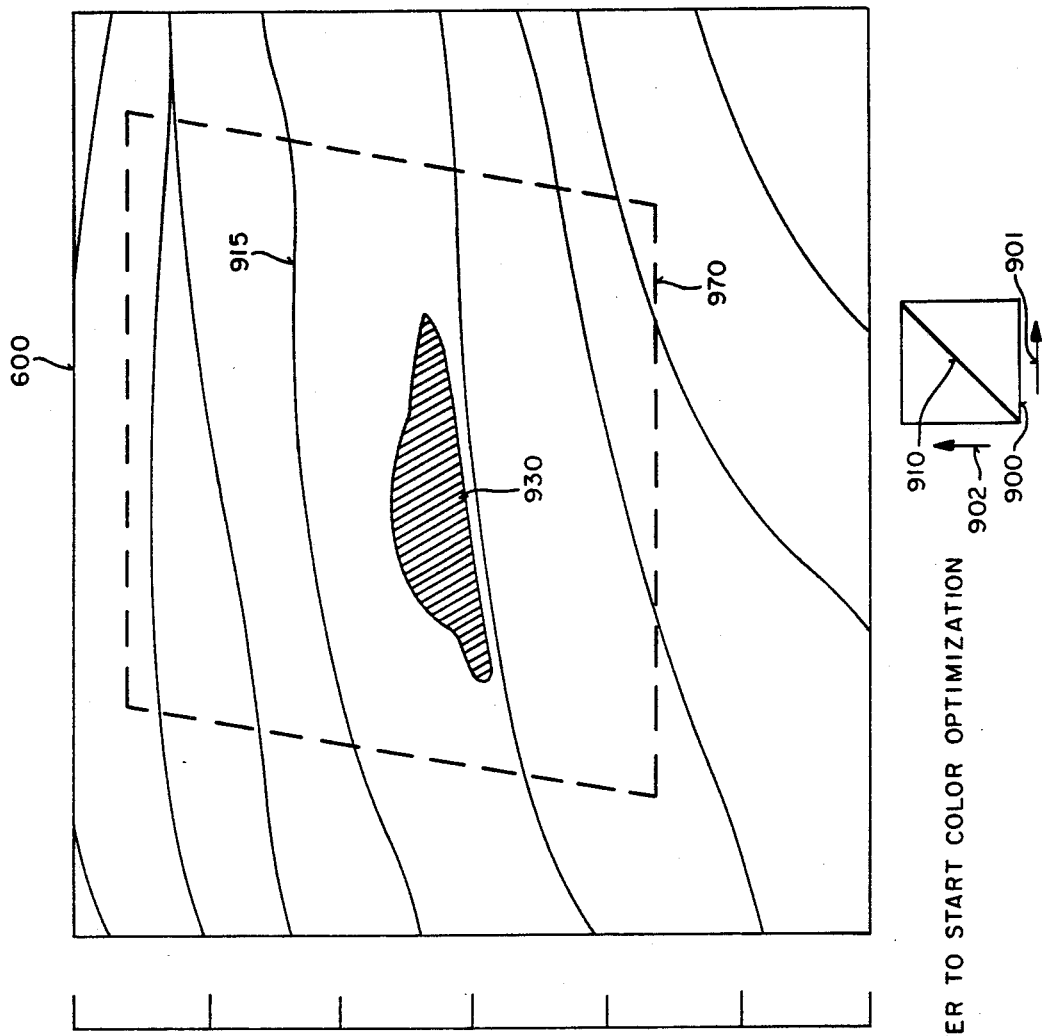
FIG_6
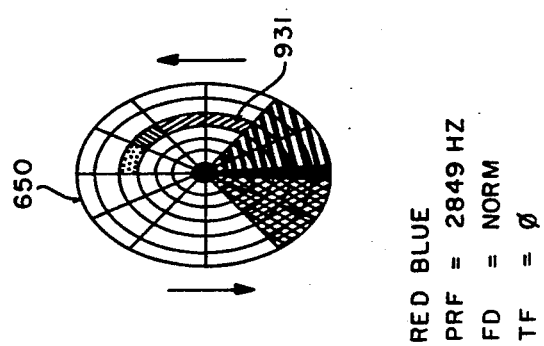

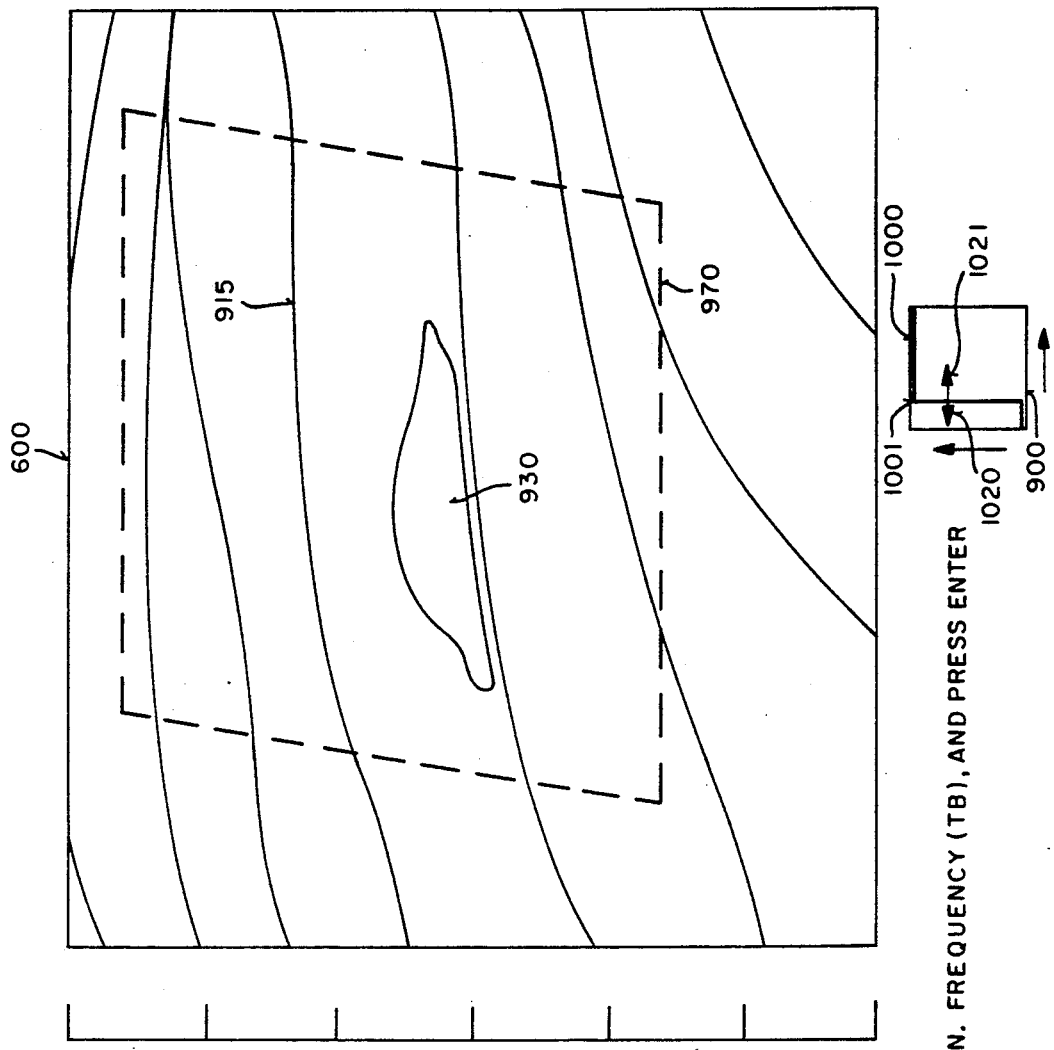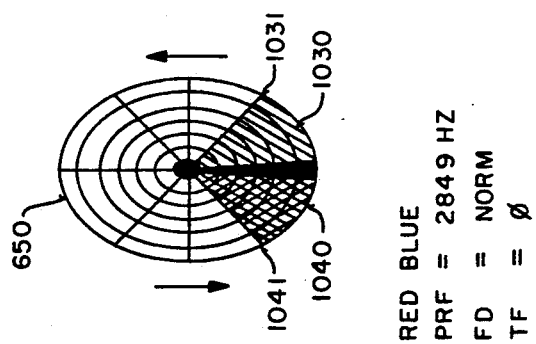

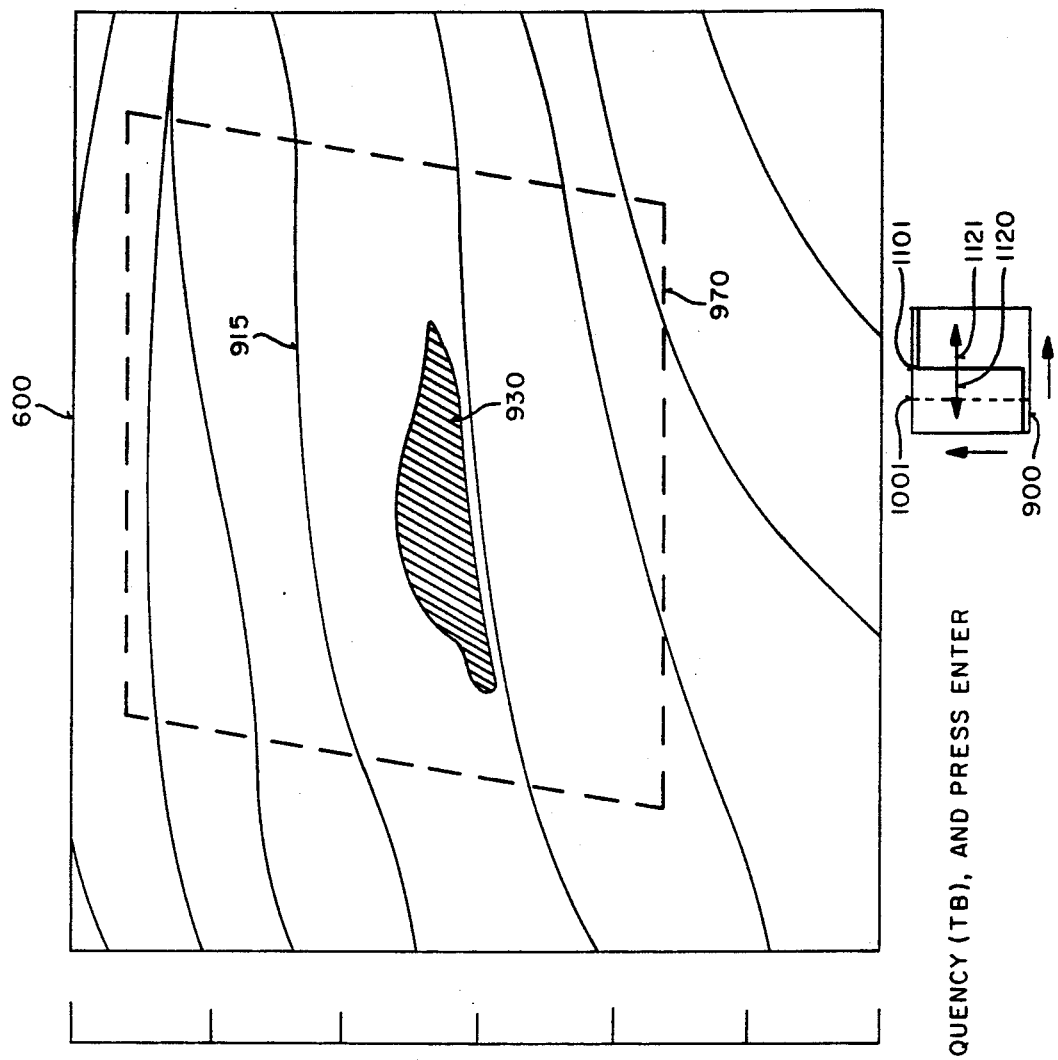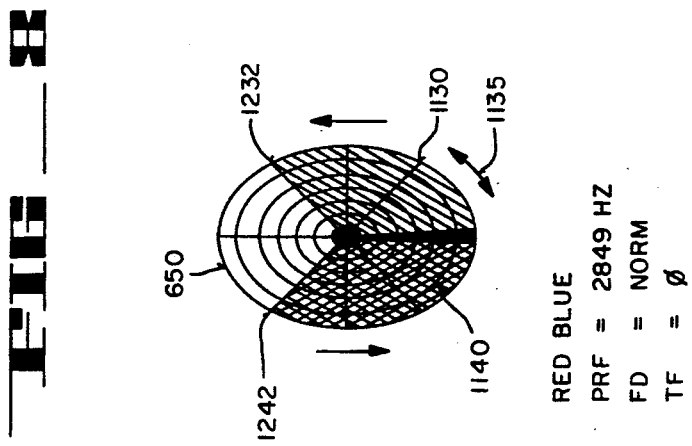

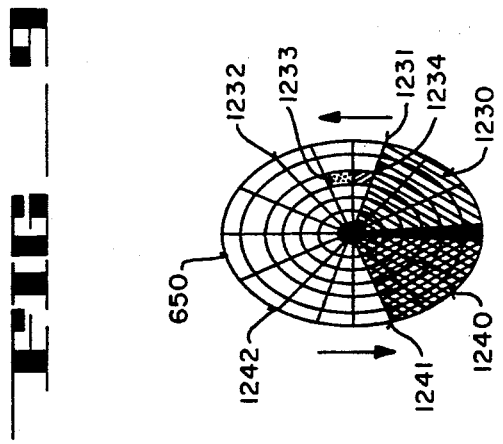
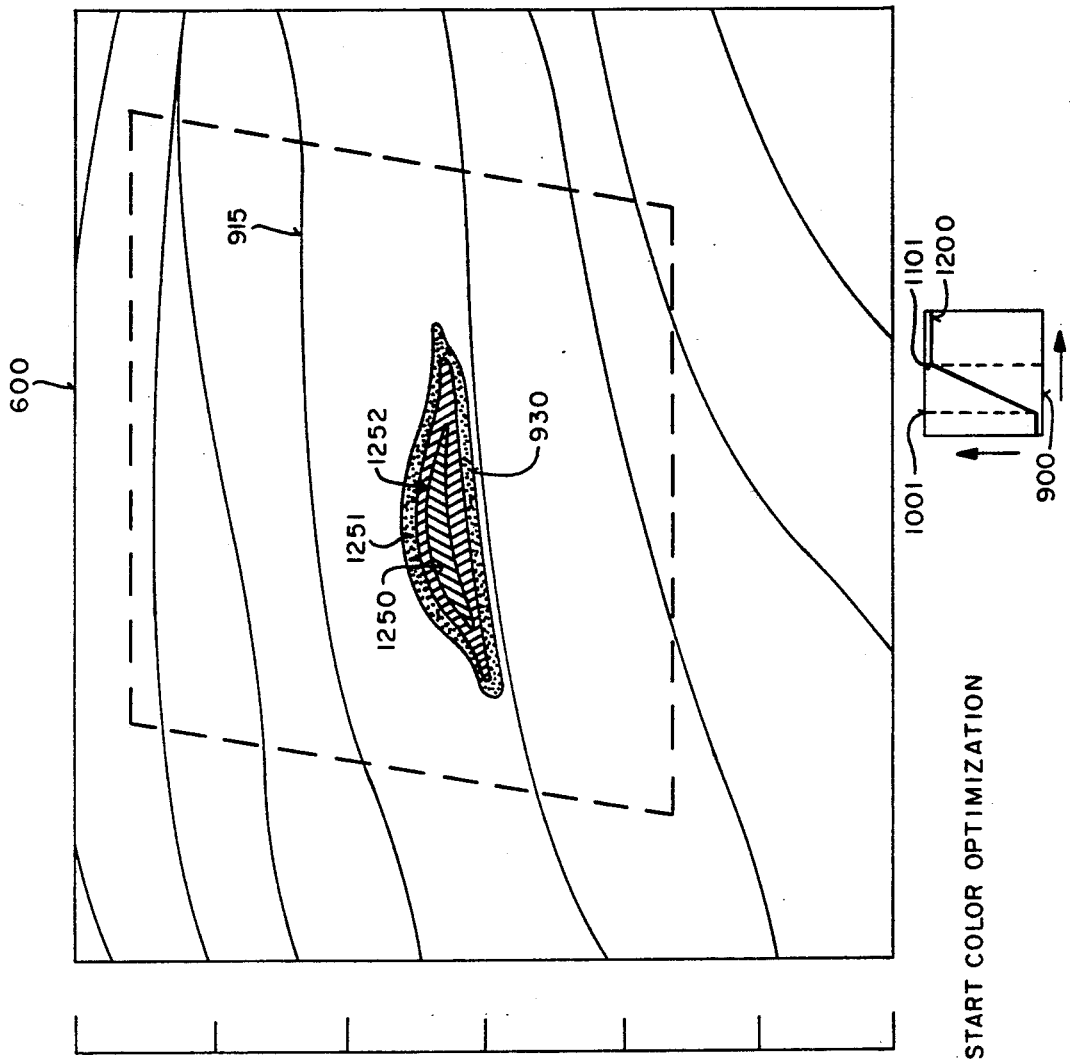
FIG_9

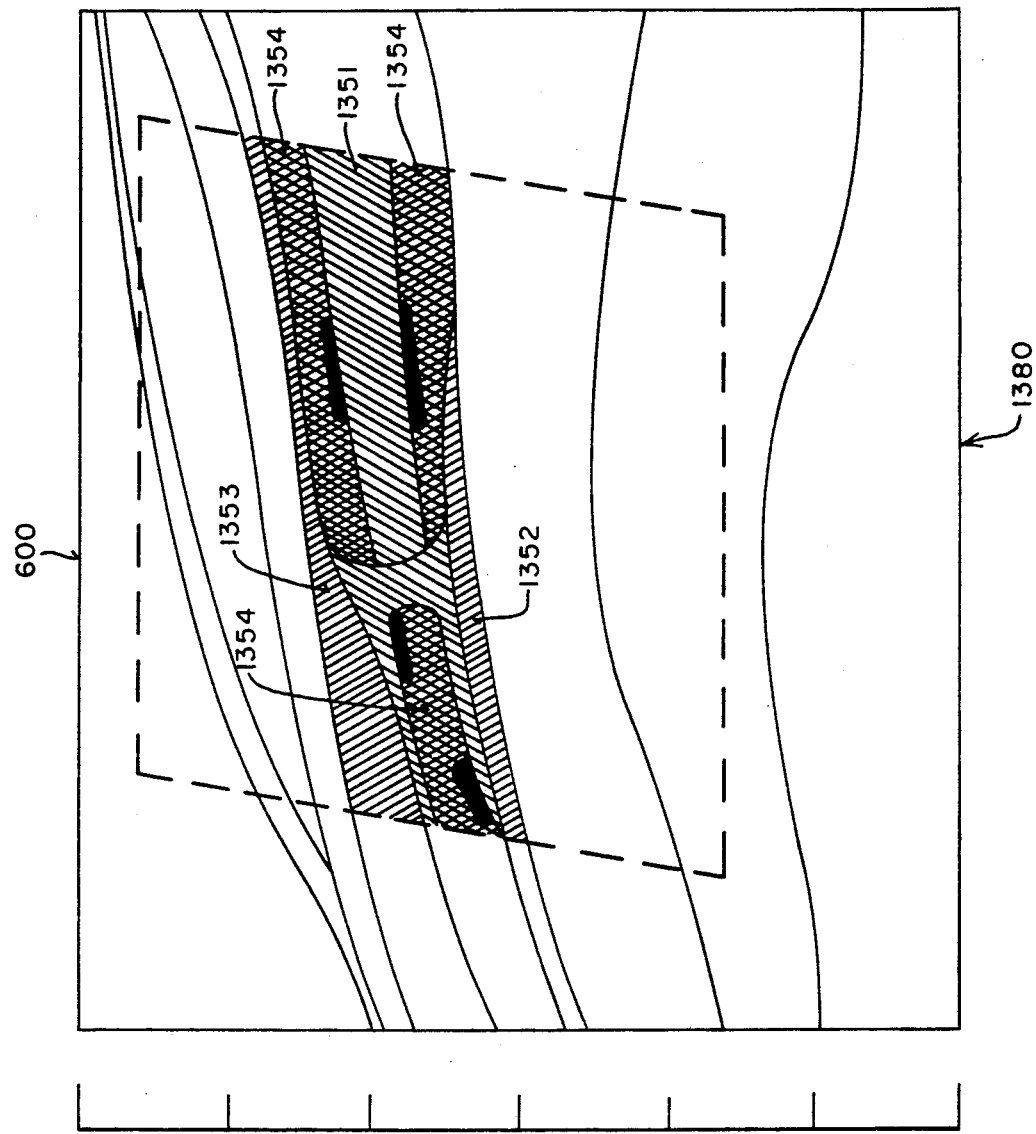
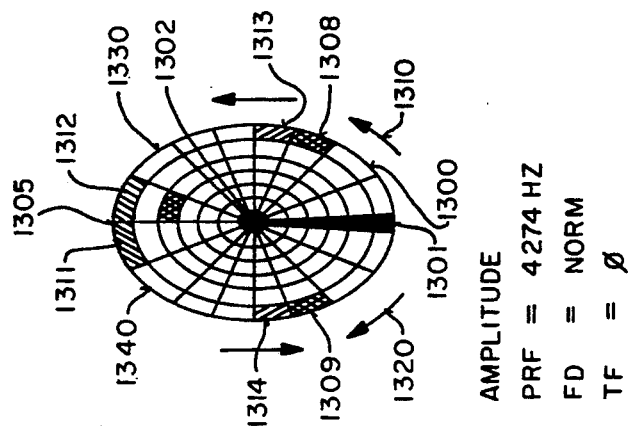
FIG_10

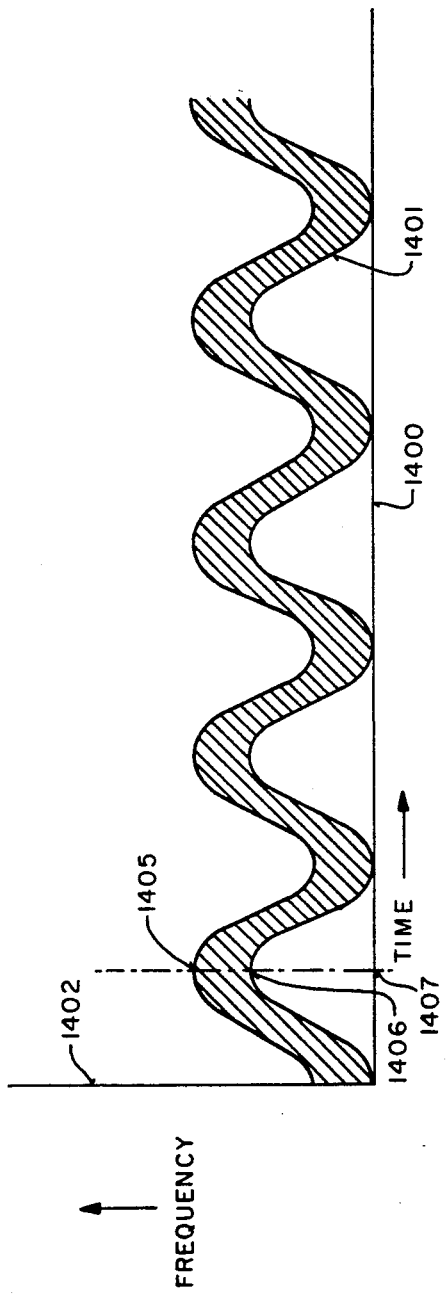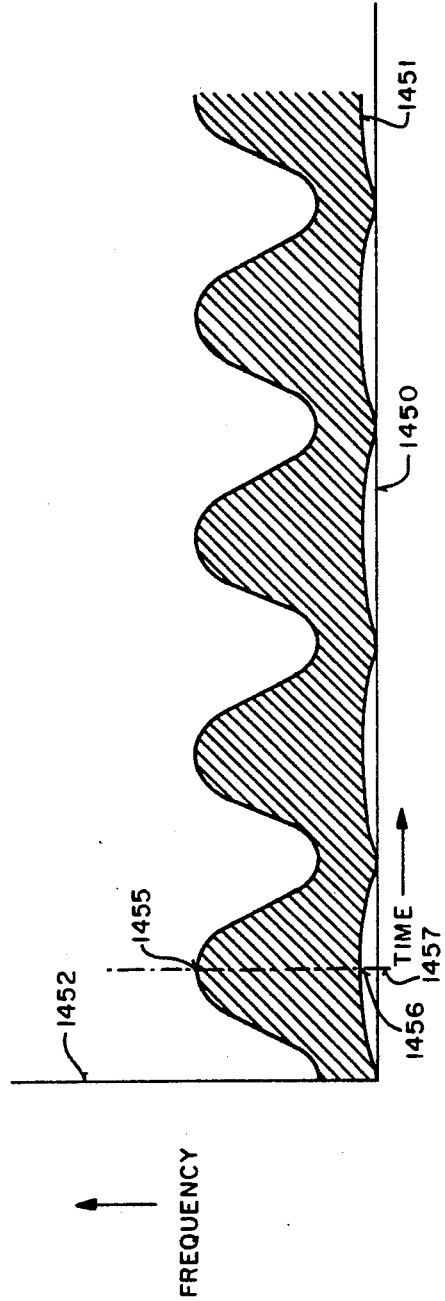

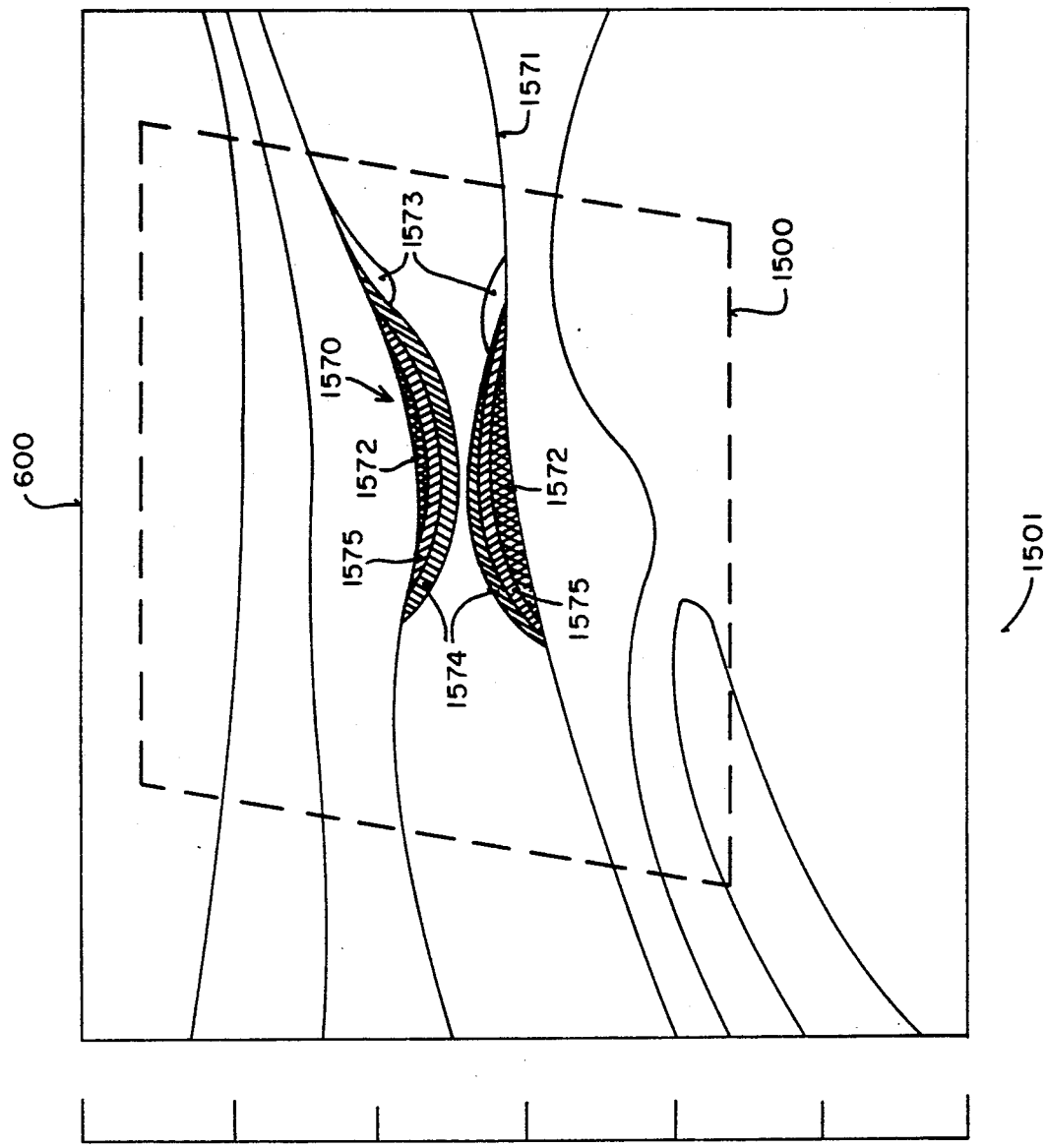
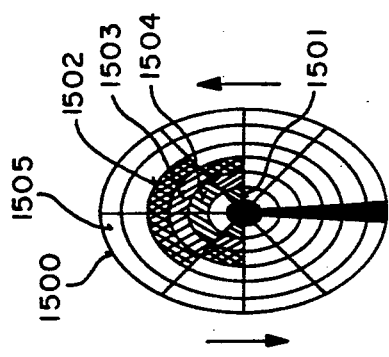
FIG_12
VARIANCE
PRF = 4274 HZ
FD = NORM
TF = ∅

APPARATUS AND METHOD FOR DISPLAYING ULTRASONIC DATA

BACKGROUND OF THE INVENTION

1. Field of the Invention

The present invention relates to the field of Doppler ultrasound imaging in living tissue. Specifically, this invention relates to an apparatus and method for display of ultrasonic data upon a video display screen for observation and diagnosis by medical personnel.

2. Prior Art

Images of living organisms typically utilize methods that pass various types of radiation through the body of the animal and measure the output with a suitable detector. For instance, x-ray images are generated by producing x-rays external to the body, passing the x-radiation through the body and observing shadows produced on x-ray sensitive film. Ultrasonic images, in contrast, are formed by producing ultrasonic waves using a transducer, passing those waves through the body, and measuring the properties of the scattered echoes from reflections inside the body using a receptor. Ultrasonic imaging apparatus may be distinguished from other medical imaging apparatus in the respect that they allow the display of soft tissues within the body which show various structural details such as organs and blood flow.

An ultrasonic imaging apparatus utilizes a probe which contains elements for transmitting Doppler pulses throughout tissue. This probe typically also contains receiving circuitry which allows reception of the reflected Doppler pulses. Some of these probes comprise a plurality of elements arranged in a linear fashion such that each of the elements can be fired at various time intervals to focus on specific parts of the body. In other systems, multiple elements are simulated by means of a moveable mechanical element within the probe wherein the Doppler pulses are transmitted at various intervals along an axis, thus simulating a plurality of elements in the probe. Each reflective pulse from the Doppler pulses emitted may then be received by a receiving unit located in the probe and transmitted to circuitry within the ultrasound apparatus for processing and generation of a display. This display, known as a b-mode image or two dimensional image of blood flow velocity, may then be generated by the apparatus and displayed on a video monitor for diagnosis and examination by an attending operator or physician.

The basic principle used in applying the Doppler method for ultrasonic imaging in a pulsed Doppler ultrasound apparatus is described as follows. When blood flow within a living subject is subjected to ultrasonic waves, corpuscles are caused to vibrate slightly while moving and reflect those ultrasonic waves. Because of the velocity of the corpuscles the frequency of the reflected waves changes from that of the transmitted waves due to the Doppler effect. The frequency shift may be detected and the amount of the shift may be displayed on a video screen for imaging blood flow in the living subject. Since the amount of shift of the transmitted waves is in relation to the blood flow velocity, the amount of blood flow and the speed of the blood flow may be observed. Noise and other signals (clutter) which have Doppler shift but don't represent blood movement in the body are filtered out. The image produced will then only represent that which is in motion. This Doppler shift frequency information is then used as blood flow information for forming a two-dimensional image or profile of the blood flow velocity.

One such apparatus used in displaying information obtained from ultrasonic pulses transmitted in the human body is shown in FIG. 1 as imaging system 100. Imaging system 100 generally comprises a probe 101 which is coupled via line 110 to transmitter/receiver circuitry 102. Transmitter/receiver circuitry 102 is designed so that the elements in probe 101 will be fired at specified time intervals, with reflective pulses being detected using probe 101 at another given time interval. Transmitter/receiver circuitry 102 is coupled to a control unit 109 via bus 120. Control unit 109 controls all circuitry in the imaging system via bus 120. Control unit 109 is further coupled to a keyboard 125 and a mouse, trackball or other device 126 for movement and control of information shown on video display 130.

Once a pulse is received by transmitter/receiver 102, such information is transmitted by line 111 to RF (radio frequency) processor 103 for further processing. This radio frequency information is further transmitted via line 114 to a graphic processor 105 and to a Doppler processor 106 via lines 114 and 113 for generation of black and white ultrasound information on video display 130. Information generated by Doppler processor 106 via in-phase (I) and quadrature (Q) signals output from RF processor 103 are transmitted via line 115 to graphics processor 105. Graphics processor 105 then integrates information received from RF processor 103 and Doppler processor 106 and then transmits scan line information to video processor 108 via line 116. In addition to information passed to graphics processor 105 and Doppler processor 106, RF processor 103 transmits I and Q signals via line 112 to color flow processor 104. Color flow processor 104 is also controlled by control unit 109 via bus 120. Color flow processor 104 is used for detecting Doppler shift and blood flow information in living tissue, and thus transmits this information via line 117 to a color scan converter 108. Such color information is used to graphically represent on video display 130 moving blood flow in a living organism. The color scan converter is used to interpolate point scan line information obtained from color flow processor 104, and transmit that information on line 118 to video processor 120 for representation of color blood flow in the human body. Video processor 120 then utilizes information obtained from graphics processor 105 for display of black and white ultrasound information and color information obtained from color scan converter 108 to generate color ultrasound information suitable for output on a video display such as 130 via line 119. Such information may be transmitted in National Television Standards Committee (NTSC) format and thus be stored on video tape for later clinical examination by attending medical personnel.

A prior art display of color Doppler ultrasound information is shown in FIG. 2 as screen 300. Screen 300 comprises a scan area 301 wherein portion 305 of scan area 301 is represented in various colors. The remainder of 301 outside 305 shows black and white ultrasound information caused by relatively stationary tissue and/or blood flow in the body being imaged. The Doppler color flow information in area 305 is shown in colors represented on scale 310 shown on the right hand portion of screen 300. One axis 321 of scale 310 represents frequency, and the second axis 320 on scale 310 represents amplitude. The range of amplitude and frequency of each pulse is represented form zero to the maximum detectable amplitude by the ultrasound receiver of probe 101 in ultrasound system 100. Frequency information is determined by measuring the phase shift of reflected waves from the pulse repetition frequency (PRF) of the reference wave. This is done, in a manner known in the art, by determining phase shift from the PRF and direction of phase shift from the PRF using I and Q signals obtained from the reflected Doppler pulses.

The frequency information shown on scale 310 will be displayed as various colors on scan region 301 according to the colors shown in scale 310. For instance, an area shown as 304 in scan area 301 may be represented in a color defined on scale 310 as 311. This area 311 may correspond with certain amplitude and frequency ranges for the reflected Doppler pulses. Likewise, other colors may further be represented on scale 310 and correspond with areas shown in scan area 305. For instance, area 304 may be represented in a color defined as being within the frequency and amplitude range shown on scale 310 as 312, and area 302 may be within the frequency and amplitude ranges shown on scale 310 as area 313. In this manner of the prior art shown as screen 300 in FIG. 2, speed and amount of blood flow information in a living organism may be clearly shown on a two-dimensional video display screen 130 for analysis.

One additional feature of the prior art system is that certain blood flow may be represented as moving towards probe transducer 101 shown in FIG. 1, and other blood flow will be shown as traveling away from probe 101 depending on the scale displayed as 310 of screen 300. For instance, one point on scale 310 such as 325, may be an origin representing blood flow with zero phase shift (zero velocity). Any regions shown in a color represented in area 326 of scale 310 may be represented as going away from the transducer, and areas shown in colors represented in area 327 may be represented as traveling towards the transducer. These colors, of course, are dependent upon whether the frequencies show a positive or negative Doppler shift from the PRF.

The choosing of a PRF is dependent upon the depth of the scan being performed, and the amount of frequency resolution required by the operator. For instance, the greater the PRF, the greater the amount of frequency resolution in the color-flow image, however, the shallower the depth of the scan. In a typical ultrasonic imaging system, each color sample volume (CSV—a horizontal row on a display), may range from approximately 0.5 millimeters to one centimeter. One aspect of the PRF is that motion of extremely high rates towards or away from the transducer generates reflected Doppler signals which are incorrectly represented on screen 300. These reflected Doppler signals may appear to be in motion away from the transducer when the blood flow is actually towards the transducer. These errors generally occur when the phase shift from the PRF is greater than 180 degrees, or the reflected signal is greater than PRF/2 (or less than −PRF/2 is the negative direction). Generally, the PRF must be twice that of the maximum frequency expected to be received to prevent this error from occurring. If the frequency of the reflected wave is greater than PRF/2, then the reflected Doppler wave will be assigned to an erroneous frequency. This error in assignment is called aliasing, and the frequencies at which aliasing occurs (±PRF/2) are known as the Nyquist limits. The Nyquist limits of the prior art system shown on screen 300 of FIG. 2 are represented as points 314 and 315. If point 315 is the positive Nyquist limit and 314 is the negative Nyquist limit for the PRF, certain reflected pulses which exceed the frequency 315 on scale 310 will appear in area 326 (the negative area) of scale 310. Although the Nyquist limit of the PRF is an inherent limitation in pulsed Doppler systems, the prior art color display shown as screen 300 in FIG. 2 does not clearly illustrate this aliasing error. Therefore, an improved method for displaying colors in an ultrasonic pulse Doppler imaging system is required which will clearly display the aliasing error. This allows an operator performing the scan to adjust the PRF, if desired, to minimize aliasing problems and maximize the resolution of displayed information.

SUMMARY AND OBJECTS OF THE INVENTION

One object of the present invention is to provide color display of ultrasonic information in real-time in such a way as to clearly show aliasing errors from a reference Doppler pulse, to allow diagnostic personnel to minimize such errors while maintaining effective diagnostic resolution of diseased tissue and blood flow.

Another object of the present invention is to provide alternative displays of ultrasound data in a manner which assists the viewing of certain conditions.

These and other objects of the present invention are provided for by a method of displaying an image comprising reflected pulsed Doppler signals in real time produced by reflecting a reference pulsed doppler signal, each reflected signal displayed in a color defined by a polar coordinate plot, wherein the polar coordinate plot comprises an origin representing a reflected signals of the reference pulsed doppler signal having zero amplitude and zero frequency. The polar coordinate plot further comprises an axis representing reflected signals of the reference pulsed doppler signal having zero frequency, a radius with respect to the origin representing amplitude information of reflected signals of the reference pulsed doppler signal, an angle with respect to the axis representing the frequency of reflected signals of the reference pulsed doppler signal, and a vector displaced 180 degrees from the axis, the vector representing a Nyquist limit of the reference pulsed doppler signal. The colors on the plot in a positive direction at a maximum amplitude for a first frequency towards a point representing maximum amplitude for a second frequency range from red to white, colors on the plot in a negative direction at a maximum amplitude for a third frequency towards a point for a maximum amplitude for a fourth frequency range from blue to white, and the colors for each frequency on the plot range from the color at a maximum amplitude for each frequency to black at the origin.

These and other objects are provided for by a method for displaying an image comprising reflected pulsed doppler signals in real time produced by reflecting a reference pulsed doppler signal, each reflected signal displayed in a color defined by a polar coordinate plot. The polar coordinate plot comprises an origin representing reflected signals of the reference pulsed doppler signal having maximum variance and an axis representing reflected signals of the reference pulsed doppler signal having zero frequency. The polar coordinate plot further comprises a radius of each color with respect to the origin representing variance information of reflected signals of the reference pulsed doppler signal, wherein the maximum radius represents reflected signals having minimum variance, and the angle of each color on the polar coordinate plot with respect to the axis representing a frequency of reflected signals of the reference pulsed doppler signal. Also, the polar coordinate plot comprises a vector displaced 180 degrees from the axis, wherein the vector representing a Nyquist limit of the reference pulsed doppler signal. The ultrasonic information is displayed in shades of green wherein green represents maximum variance information and black represents minimum variance information according to the polar coordinate plot.

BRIEF DESCRIPTION OF THE DRAWINGS

The present invention is illustrated by way of example and not limitation in the Figures of the accompanying drawings in which like references indicates similar elements and in which:

FIG. 3 shows a red/blue color Doppler display of blood flow used in the preferred embodiment along with a color wheel map.

FIGS. 4A and 4B show how the color wheel of the preferred embodiment may correspond with a color scale used in a prior art ultrasonic imaging apparatus.

FIG. 5 shows the distribution of colors in color wheel of the preferred embodiment.

FIGS. 6–9 show the steps used in remapping the frequency range of the color wheel of the preferred embodiment.

FIG. 10 shows an amplitude-only display of ultrasonic images with a color wheel map.

FIGS. 11A and 11B show spectral traces of reflected Doppler pulses versus time, one display with low variance and the other with high variance.

FIG. 12 shows how variance information may be represented in a blood flow display using the color wheel of the preferred embodiment.

DETAILED DESCRIPTION

Figure 1:
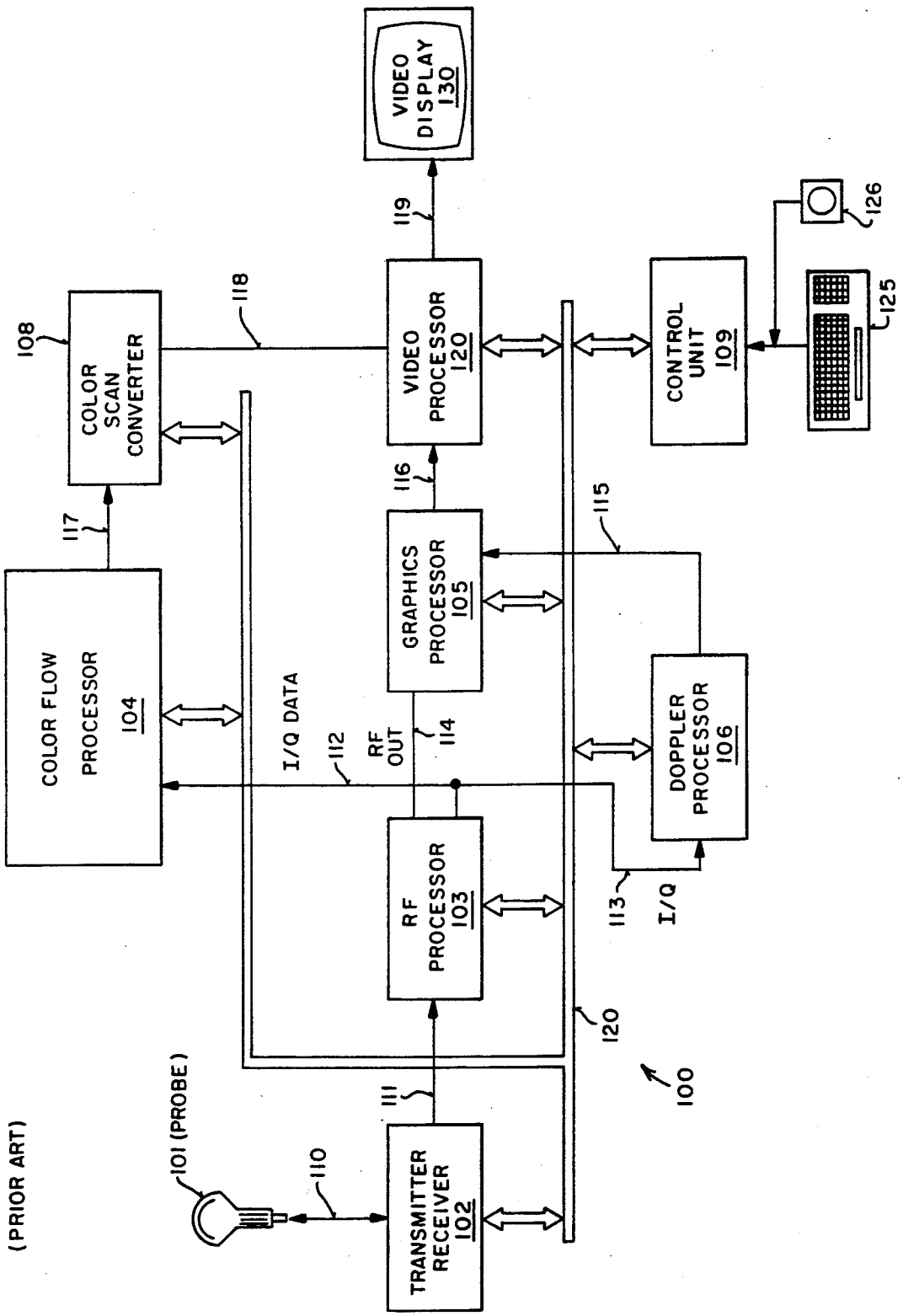
FIG. 1 shows a prior art ultrasonic imaging system.

The present invention covers a method and apparatus for acquiring ultrasonic imaging data, and displaying that data on a suitable video display screen. In the following description, numerous specific details are set forth such as colors used, specific hardware components, etc., in order to provide a thorough understanding of the present invention. It will be obvious, however, to one skilled in the art that these specific details may not be required to practice the instant invention. In other instances, well-known components of ultrasonic imaging apparatus have not been described in detail to not unnecessarily obscure the present invention.

Referring to FIG. 3, ultrasonic information obtained from color flow processor 104 and color scan converter 108 via line 118, is displayed by video processor 120 in the preferred embodiment as image 600 on video display 130. As shown on video display 600 of FIG. 3, a region of interest 610 may be selected by an operator for the display of color ultrasound information. Generally, ultrasound information outside region of interest 610 on screen 600 is shown in a gray scale format. Generally, those objects inside region of interest 610 which are not moving or are moving at a very slow rate and thus have very little detectable phase shift from the PRF will also be displayed in gray scale. As shown in region of interest 610, a blood vessel such as 620 may be displayed in color. Each of the shaded areas shown in 610 are displayed in color and are representative of certain frequency phase shifts from the PRF for screen 600.

Notice that screen display 601 further comprises a color wheel 650 which contains certain colors corresponding with colors displayed in region of interest 610. Color wheel 650 is a polar coordinate plot containing colors for certain frequency and amplitude ranges. The angle of each vector on color wheel 650 represents, in the preferred embodiment, frequency (velocity) for reflected signals. The radius of each color on color wheel 650 represents amplitude information (strength of signal) for reflected signals. For each color displayed in region of interest 610, the same color is shown on color wheel 650. The frequency and amplitude of the reflected wave in region of interest 610 can be determined by referring to the position of the color on color wheel 650. In the preferred embodiment, color wheel 650 is elliptical in shape, however, any somewhat circular shape may be used for color wheel 650 in alternative embodiments. As shown on FIG. 3, region 611 is represented in a color shown on color wheel 650 as 661. Likewise, regions 612 are represented in a color shown in region 662 on color wheel 650, and region 613 on display 600 is shown in a color represented on color wheel 650 as 660. Finally, region 614 on display 600 is shown on color wheel 650 as 663.

Note that each color on color wheel 650 represents a specific frequency and amplitude for a reflected signal shifted from the PRF. Colors on the right side of color wheel 650 in the preferred embodiment are shown in shades of red, and are represented as frequencies red-shifted from the PRF (indicating motion towards probe 101). This is indicated by the vertical arrow 690 pointing upwards as shown on display 601. Conversely, colors such as 663 which are on the left side of color wheel 650 are represented in shades of blue. These are frequencies that are blue-shifted from the PRF (indicate motion away from probe 101). This is indicated by vertical arrow 680 pointing downwards. A more detailed description of the color wheel's mapping for a display such as on screen 600 is discussed with reference to FIGS. 4A and 4B.

Figure 2:
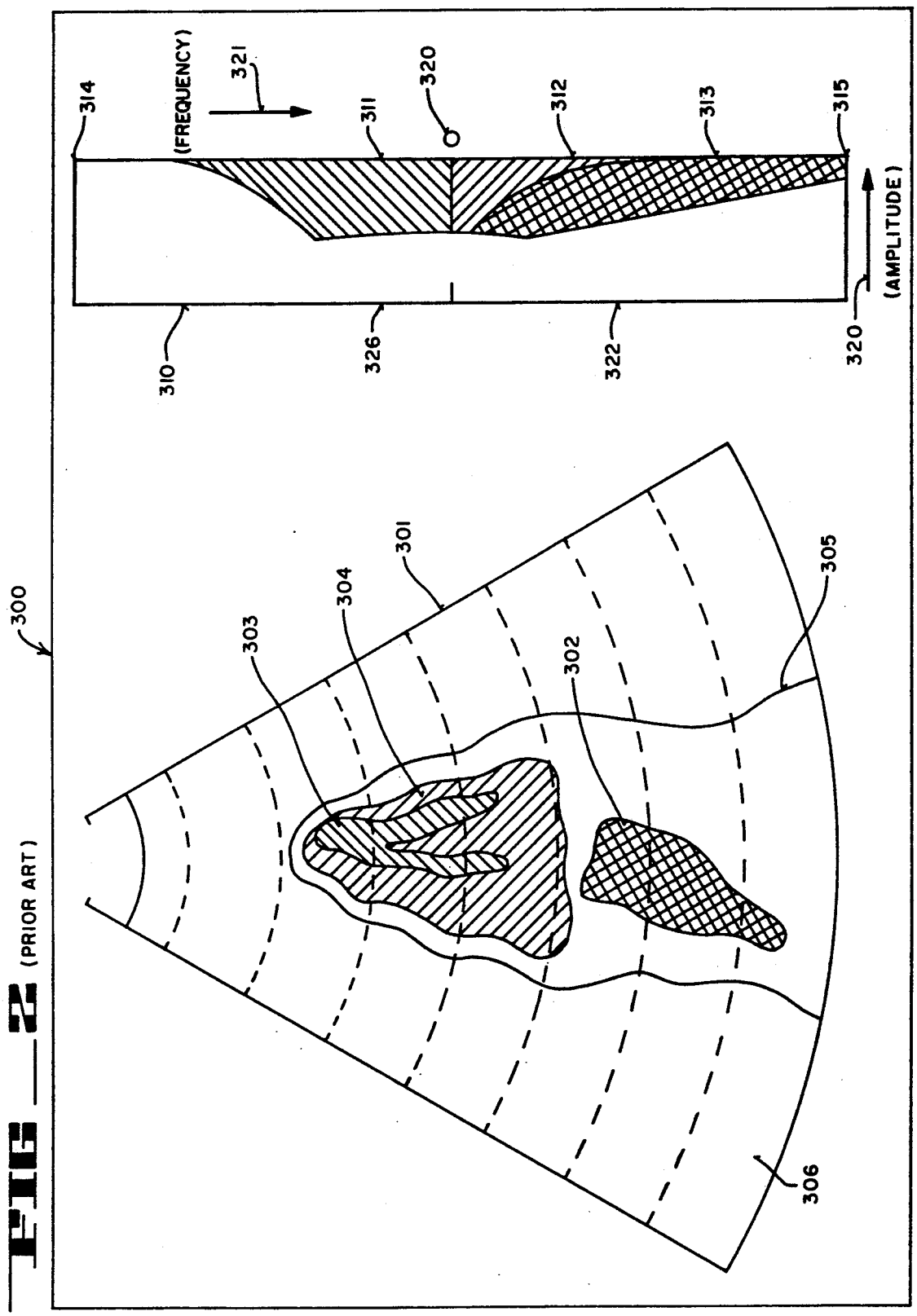
FIG. 2 shows a prior art color display of ultrasonic imaging data used to represent reflected Doppler pulses.

The mapping of colors to frequencies and amplitudes on color wheel 650 is shown in more detail and discussed with reference to FIGS. 4A and 4B. Shown in FIG. 4B is a prior art color scale 700 which is similar to scale 310 of FIG. 2. As shown in 650 of FIG. 3, a given series of colors, such as those used to represent region of interest 610 in FIG. 3, may be mapped to a polar coordinate scale. 650 may correspond with certain frequencies and amplitudes shown on a prior art scale such 700. In the preferred embodiment, the angle of a vector intersecting a color, such as 600, represents the frequency of a reflected wave which has been shifted from the PRF. The shift of the reflected wave is positive if the color lies between points 710 and 720 in direction 740 on wheel 650, or is negative if it lies between points 710 and 720 in direction 750.

The radius of the position of the color for color wheel 650 represents the amplitude of the reflected wave. Small amplitudes are represented by colors residing at small radii in color wheel 650 (with origin radius 711 having zero amplitude) and colors indicating larger amplitudes residing at larger radii. As shown in FIG. 3, an area such as 613 which is displayed in the color represented in region 660 of color wheel 650, has a certain frequency and amplitude as determined by the color's location on color wheel 650. The same color may be represented on a prior art map such as 700 wherein a horizontal axis such as 771 represents frequency information, and a vertical axis such as 772 represents amplitude information. As mentioned above, each color on color wheel 650 shown from point 730 to point 733 in direction 740 is represented in a shade of red since it represents frequencies that are red-shifted from the PRF. Conversely, colors on color wheel 650 between points 731 to 732 in direction 750 are shown in shades of blue representing blue-shifted frequencies from the PRF.

Also shown on color wheel 650 is origin 711 and origin vector 710 which represent the extreme low amplitude and low frequency ranges for the colors of reflected pulses, respectively. Below certain frequency phase-shifts such as minimum frequencies 730 and 731 on scale 650, information that is received generally tends to be clutter (noise or stationary objects) so it is filtered out. Any phase shifts detected below 730 and 731 are not displayed and are instead represented in black in region 710 (an origin vector) on color wheel 650. Likewise, no meaningful amplitude information is available below a certain amplitude. As shown in region 711, black (no color) is used to represent signals having amplitudes less than a given level. The amplitude information in this area for certain reflective pulses is generally clutter.

As discussed above, very fast motion of blood may generate aliasing errors. In other words, some blood flow may be shown as moving the opposite direction than it is actually moving. Aliasing errors will tend to be large for small PRFs and will decrease for larger PRFs. The larger the PRF, however, the less the resolution of the resulting display. As shown in prior art scale 700, an extremely fast blood flow such as that shown in region 614 of FIG. 3, may erroneously be represented as an extremely blue-shifted blood flow. This region's frequency is shown in a color represented in area 763 of scale 700 shown in FIG. 4B. It is known that blood flow in the center of an artery such as 620 in FIG. 3 has a higher velocity than the blood flow at the edges. So, the operator of ultrasound imaging apparatus 100, when viewing the image shown in 600 of FIG. 3, may realize that region 614 is in fact a very fast blood flow that is causing aliasing. Corrective measures may then be taken such as increasing the PRF, thus showing region 614 as a properly red-shifted display. However, when using a scale such as 700 in FIG. 4B, this aliasing error will not be clearly illustrated since the color will be represented as having a negative phase shift, such as shown in area 763, when in fact it is probably a very large positive phase shift. Color wheel 650 can actually be viewed as a flat scale such as 700 wrapped upon itself (where positive and negative Nyquist limits 760 and 770 are touching). Color wheel 650, in contrast to prior art scale 700, will have only one Nyquist limit vector 720 (±PRF/2). Aliasing can be clearly observed on color wheel 650 by noting colors that are represented clockwise (for a negative aliased phase shift) or counterclockwise (for a positive aliased phase shift). If aliasing is suspected it may be confirmed by reference to color wheel 650.

For instance, if given blood represented in a color such as 761 on scale 700, when the blood is accelerated to a velocity causing a phase shift just beyond Nyquist limit 720, then the same blood flow for the same amplitude would be represented as extremely blue-shifted blood flow on scale 700 in the color shown as 763. Color wheel 650 clearly illustrates this type of aliasing error. For instance, as shown in FIG. 3, the blood flow shown in area 614 of display 600 corresponds with the color shown in region 663 of color wheel 650 in FIGS. 3 and 4A. This color is probably a faster moving blood flow than that shown in regions 612 of screen 600 because region 614 is in the center of the artery and it is known that blood flows faster in the center of an artery than at the sides such as shown in areas 612. The operator can then readjust the PRF to clearly show region 614 in a color indicating red shift. Alternatively, the operator might merely take note that region 614 is extremely fast moving blood flow which generates frequencies beyond the Nyquist limit. The advantage of the preferred embodiment's method of representing color data is that the positive and negative Nyquist limits intersect. Thus, the aliasing error that occurs at Nyquist limit 720 on color wheel 650 is clearly illustrated by a color counterclockwise from the Nyquist limit when the limit is exceeded by a fast velocity in the positive direction. Likewise, a negative velocity generating a frequency below the negative Nyquist limit may be clearly illustrated in a color clockwise from Nyquist vector 720. In contrast, the aliasing occurring at positive and negative Nyquist limits 760 and 770 on prior art scale 700 is obscured since it is not clear whether the frequency shown is actually a negative phase shift, or an extremely fast moving blood flow generating a positive phase shift. It can be appreciated that the preferred embodiment's representation of colors in this circular fashion conveys more information than the prior art system.

To clearly illustrate the red and blue shifting from the PRF on display 601, colors are represented on color wheel 650 in counterclockwise direction 740 from 730 to Nyquist limit 720 in shades of red. In the preferred embodiment, the maximum amplitude at the frequency just before the Nyquist limit (points 733), the color will be the minimum saturation and maximum luminance value (white). Wheel 650's color will range from this color to the maximum saturation of red at point 730. Intermediate colors for the maximum amplitude around color wheel 650 in direction 740 will be represented as shades of red between those two values. Conversely, in direction 750 (representing blue-shifting) from point 731 to point 732 (at the maximum amplitude), the color will range from maximum saturation for blue at point 731 to maximum luminance and minimum saturation at point 732 (white). Further, as the amplitude decreases on color wheel 650 (the radius decreases), the luminance of the color decreases. Luminance and saturation are a minimum at origin 711 and origin vector 710. In summary, on color wheel 650, luminance is a function of amplitude and saturation is a function of frequency. Luminance is a maximum at Nyquist vector 720 for the maximum amplitude. Saturation is a maximum at a point just beyond the origin vector 710 (points 730 and 731), and a minimum at the Nyquist limit vector 720. It can be appreciated from the foregoing that many colors may therefore represent the frequency and amplitude range of imaging system 100. A unique color may therefore be generated for each frequency and amplitude displayable on color wheel 650. Since each color on a display such as 600 of FIG. 3, corresponds with a certain frequency and amplitude range, in the preferred embodiment, the frequency and amplitude of each signal may be determined by referring to the same color on color wheel 650.

Because the sensitivity of system 100 increases as the amplitude (strength) of the Doppler signal increases, the number of colors in the preferred embodiment representing each frequency at each amplitude can also increase on color wheel 650 to show more information. FIG. 5 shows the actual number of colors present on color wheel 650 in the preferred embodiment. Once the amplitude reaches a certain minimum value, those amplitudes are represented in a certain number of colors. For instance, at radius 830 (the minimum amplitude displayable in color) shown in FIG. 5, the frequencies for reflected pulses are represented in two colors only. Therefore, reflective pulses having a minimum amplitude defined by ring 830 and any red-shift (region 831) will be represented in one shade of red. Conversely, any reflective pulses having blue-shifting at amplitude 830 (region 832), will be represented in one shade of blue. The maximum displayable amplitude, such as that represented at ring 800 of color wheel 650, will be represented in 32 colors (16 for the range of the blue-shifted frequencies, and 16 for the range of the red-shifted frequencies, respectively). Each ring towards the center progressively has fewer colors which may represent the frequencies at the amplitude. For instance, at the amplitude represented at ring 810, only 30 colors are represented (15 for red and blue-shifted frequencies, respectively). At amplitude represented by ring 820, 24 colors are present (12 for red and blue-shifted frequencies, respectively), at ring 840 18 colors are present (9 for red and blue-shifted frequencies, respectively), 12 for those frequencies at the amplitude represented by ring 850 (6 for red and blue-shifted frequencies, respectively), and for frequencies represented at the amplitude represented by ring 860 of color 650, there are only 6 colors present (3 for red and blue-shifted frequencies, respectively). Thus, there are a total of 122 colors available for display on an ultrasonic image on video display 130.

OPTIMIZING COLORS

The 122 color range on color wheel 650 may also be optimized (re-mapped) for certain frequencies shown in fewer colors on display 600. This will enhance the detail for certain frequency ranges that the operator of ultrasonic imaging apparatus 100 finds interesting. For instance, as shown in FIG. 6, a new region of interest 970 may be displayed on screen 600. Region 970 shows a portion of blood vessel 915 and has an area 930 which is represented in only one color shown corresponding with the amplitudes and frequencies for the area 931 shown on color wheel 650. Area 930 may be viewed as interesting and a clinician may desire to enhance the detail within that region. In order to enhance the detail, a remapping of the color range for the frequencies contained within area 930 for color wheel 650 may be performed which will show region 930 with more than one color. This optimization is shown and discussed with reference to FIGS. 6 through 9.

The first step in remapping the frequencies vs. colors for area 930 is shown in FIG. 6. First, the user will indicate to system 100 that color optimization of wheel 650 is required. This is done by depressing, in the preferred embodiment, an appropriate key on keyboard 125 of system 100 shown in FIG. 1. As shown in FIG. 6, mapping display 900 will appear showing a color vs. frequency graph. Curve 910 represents the current frequency vs. color mapping used on color wheel 650. Horizontal axis 901 represents the currently displayable frequency range (0 to PRF/2), and the vertical axis 902 represents the current color range. Message 950 indicates that once the user depresses the "Enter" key on keyboard 125, color optimization will start. Once the "Enter" key is depressed, the display will change to correspond with that shown in FIG. 7.

The next step in the color optimization process is shown in FIG. 7. Once color optimization is started, message 1050 is displayed on video display 130. 1050 requests entry of the minimum frequency on color wheel 650 for the new color range. Once selected, display 900 now indicates at point 1001 the minimum frequency at which the maximum saturated color will be displayed. This is the point where the colors will begin to be distinguished on color wheel 650. The minimum frequency will be adjustable by moving an input device, in the preferred embodiment such as a trackball or mouse 126 shown in FIG. 1, in the horizontal directions 1020 and 1021 on display 900 to move minimum frequency 1001 as shown in FIG. 7. As trackball 126 is moved and point 1001 of 900 moves in directions 1020 and 1021, vectors 1031 and 1041 will move radially about color wheel 650 to correspond with the positive and negative values of the minimum frequency 1001 currently selected. For instance, if the frequency 1000 Hz was represented at 1001, then the color from origin vector 710 on color wheel 650 to vector 1031 (representing 1000 Hz) would be represented in only one color, the maximum saturation of red (region 1030). Likewise region 1040 from origin vector 710 to vector 1041 (−1000 Hz) on color wheel 650, would be represented in the maximum saturation of blue.

Once the minimum frequency has been determined, the user of system 100 must determine the maximum frequency range for which the color range is to be mapped. This step is shown in FIG. 8. Message 1150 prompts the user to locate the maximum frequency for color wheel 650 on display 900 for which the color range is going to be mapped. Note minimum frequency 1001 is now shown as a vertical dashed line on display 900. Notice also that there is a second point 1101 of curve 1100 for which the maximum frequency of the 122 possible colors is represented. As with minimum frequency 1001, trackball 126 may used to move maximum frequency 1101 horizontally in directions 1120 and 1121 to define the maximum frequency displayable. As this is done, vectors 1141 and 1131 move radially in directions 1135 around color wheel 650 such that areas 1140 and 1130 become larger and smaller depending on maximum frequency 1101. Note that as the frequency range for maximum frequency 1101 encompasses the frequencies currently represented in region 930, region 930 will change to the color shown in region 1130 on color wheel 950. Once maximum frequency 1101 has been defined, the user then depresses the "Enter" key on keyboard 125 in the preferred embodiment. System 100 then remaps the displayable color range to the frequencies indicated as the minimum and maximum. In addition, the color values for the range are recalculated (optimized) for this new frequency range between minimum frequency 1001 and maximum frequency 1101.

Once the color range is remapped, as shown in 900 of FIG. 9, curve 1200 now represents the current frequency vs. color mapping which is displayed on color wheel 650. Message 950 again prompts the user to redefine color wheel 650, if desired. Note that the minimum frequency for the maximum saturation and luminance of the colors is now shown as 1001 as in the earlier figures, and the maximum frequency representing the minimum saturation for each color is now represented at point 1101 as shown on display 900 of FIG. 9. Between vectors 1231 and 1232 in the positive direction the full red color range is mapped. Also between vectors 1241 and 1242 in the negative direction, the full blue color range is mapped. As a result of this optimization, the detail within the feature 930 on display 600 has now been enhanced. For instance, area 1250 is now represented in a color shown by the frequency and amplitude in region 1230, or an area below the new color mapping range (vector 1001). Area 1251 on display 600 is now represented in a color shown on color wheel 650 as 1233, and area 1252 is represented in a color represented in an area 1234 of color wheel 650. As a result of the foregoing operation, the detail in region 930 has now been enhanced. This provides more information to an attending physician for diagnosis of diseased tissue which may be present and indicated by the blood flow shown in area 930.

AMPLITUDE-ONLY DISPLAY

Referring to FIG. 10, an alternative embodiment of the present invention is shown wherein color wheel 1300 represents amplitude-only information. All of the colors in color wheel 1300 are now represented in shades of magenta, instead of red and blue. Positive and negative phase shift information has been eliminated. In display 600 shown in FIG. 10, each of the colors in region of interest 1310 are represented in various shades of magenta according to amplitude-only color wheel 1300. Color wheel 1300, like color wheel 650, represents frequency information as the angle of the vector offset from the origin vector 1301. Also, each radius extending out from a center 1302 represents amplitude information. There is an increase in luminance in both directions 1310 and 1320 from origin vector 1301 until the maximum luminance for magenta is reached at the outer ring at Nyquist limit vector 1305. In addition, luminance is a function of amplitude and ranges from a minimum at central origin 1302 to the maximum luminance for a given frequency at the outer ring, such as Nyquist limit vector 1305.

As can be appreciated from color wheel 1300, the two halves 1330 and 1340 of color wheel 1300 are also symmetric with respect to one another. That is, a given shade of magenta will be represented as the same shade as magenta on the opposite side of color wheel 1300. Region of interest 1310 then will display colors corresponding with color wheel 1300 without showing positive or negative Doppler shift information. For instance, areas 1352 and 1353 may be represented in colors shown on color wheel 1300 at positions 1313 and 1314. Area 1351 may be represented in the color shown at areas 1311 and 1312. Further, areas 1354 may have a specific amplitude represented on color wheel 1300 at positions 1308 and 1309. The amplitude-only display shown as screen 1380 in FIG. 10 may have a specific clinical application such as representing the efficiency of a heart pumping certain volumes of blood through a blood vessel. A display like that enclosed within the region of interest 1310 on display 600 may be generated to show this information without red or blue shift information. In the preferred embodiment, the shades of color represented in wheel 1300 are magenta, but in alternative embodiments, the color may vary accordingly.

VARIANCE-ONLY COLOR DISPLAY

Additionally, color wheel 650 may be used to represent variance information in a given blood flow. Variance is represented as the difference between a signal having the lowest velocity (phase shift) and a signal at the same point having the highest velocity (phase shift). As shown in FIGS. 11A and 11B, examples of low variance and high variance are shown. 1400 of FIGS. 11A and 1450 of FIG. 11B are representative of spectral traces of velocities over time. The horizontal axes 1401 of 11A and 1451 of 11B represent time and the vertical axes 1402 and 1452 represent frequency phase shifts from the PRF. Each of the curves 1400 and 1450 represent blood flow in a living organism. The curves show blood flow according to heart beats at one location. As is shown in 1400 of FIG. 11A, at a given point 1407 two particular points 1405 and 1406 may represent signals having a maximum velocity and minimum velocity for blood flow at a particular time for the area. Such a display as 1400 will show a narrow bandwidth for blood flow, or low turbulence, and therefore a low variance. In contrast, for a given time 1457, display 1450 of 11B will have a given maximum frequency 1455, and a minimum frequency 1456 at time 1457. The difference between maximum frequency 1455 and minimum frequency 1456 is much greater than that in 1400 for the region. Curve 1450 therefore has a higher bandwidth, or a higher turbulence and therefore a higher variance than the curve given in 1400. This turbulence or high bandwidth information may indicate disease or an obstruction in a blood vessel. This information is displayed independent of a standard red/blue or amplitude-only Doppler display as shown in earlier figures.

Referring to FIG. 12, 1501 shows an example of a variance-only Doppler display. Display 600 now shows a region of interest 1500 which contains a blood vessel 1571 showing variance information according to color wheel 1500. Color wheel 1500 will map color in a manner reversed from the amplitude-only and the red/blue Doppler shift displays. That is, radius information in color wheel 1500 will represent degrees of variance, however, origin 1501 will represent the greatest amount of variance displayable. The angle of a vector at a particular point will represent the average frequency for the Doppler shifted signals at that point. The color mapping is accomplished wherein the higher variance values shown at the center are represented in a maximum saturation of green and the lower variance values are represented on color wheel 1500 with lower saturation and luminance values. The outer-most rings of the color 1500 such as 1505 will be represented in black (no saturation or luminance and therefore no variance). For instance, with reference to region of interest 1550 in FIG. 12, showing variance in blood vessel 1571, region 1573 may have high variance values represented in a color which corresponds with area 1501 on color wheel 1500. Regions 1574 may correspond with a color shown in area 1504 (lower variance) on color wheel 1500, regions 1575 may have variance values associated with the color shown at area 1503 in color wheel 1500 (even lower variance) and 1572 may correspond with the color area 1502 (very low variance). The variance shown in blood vessel 1571 may be caused by an obstruction or blockage on blood vessel 1571 such as 1570 which may be caused by disease. Therefore, this type of variance display is useful for some types of clinical applications. Since the variance information is shown in a manner inverted from that of the amplitude-only and the red/blue displays discussed above, a variance display such as shown in FIG. 12 may be displayed simultaneously with an amplitude-only and a red/blue display as shown in FIGS. 6-14. This type of display may provide a rich amount of data, indicating blood flow velocity and amplitude, as well as variance information according to a display such as that shown in FIG. 12.

As discussed above, the circular fashion in which the color coding has been mapped in the preferred embodiment for the red/blue, amplitude-only and variance displays is a vast improvement over the prior art's rectangular coordinate system because it clearly shows the aliasing effect of an ultrasonic pulsed Doppler imaging system, whether displaying Doppler shift, amplitude only or variance information.

In the foregoing specification, the invention is described with reference to specific embodiments thereof. It will, however, be evident that various modifications and changes may be made thereto without departing from the broad scale or spirit of the invention as set forth in the appended claims. The specification and drawings are, accordingly, regarded in an illustrative rather than a restrictive sense.

What is claimed is:

1. A method of displaying reflected pulsed doppler signals in real time produced by reflecting a reference pulsed doppler signal, comprising the following steps:
    a. displaying a first set of reflected signals in a first set of colors specified by an ellipse wherein the frequency of each of the first set of reflected signals with respect to the reference pulsed doppler signal indicates relative motion towards an emitter of the reference pulsed doppler signal, the amplitude for each of the first set of reflected signals being a maximum, and each of the first set of colors in the ellipse increases in brightness radially around the ellipse in a first direction as the frequency of the each of the first reflected signals increases, reaching a maximum brightness at a first position on the ellipse, the first position representing a Nyquist limit of the reference pulsed doppler signal;
    b. displaying a second set of reflected signals in a second set of colors specified by the ellipse wherein the frequency of each of the first set of reflected signals with respect to the reference pulsed doppler signal indicates relative motion away from the emitter of the reference pulsed doppler signal, the amplitude for each of the first set of reflected signals being a maximum, and each of the second set of colors in the ellipse increases in brightness radially around the ellipse in a second direction as the frequency of the each of the first reflected signals increases, reaching a maximum brightness at the first position on the ellipse; and displaying a third set of reflected signals in a third set of colors, the third set of colors ranging from the colors for each of the first set of signals and the second set of signals, to a minimum saturation of the colors at the center of the ellipse.

2. A method of displaying an image comprising reflected doppler display signals in real time produced by reflecting a reference pulsed acoustic signal, each reflected doppler display signal being displayed in a color defined by displaying a polar coordinate plot comprising the following steps:
    a. displaying an origin of the polar coordinate plot representing reflected signals of the reference pulsed acoustic signal having zero amplitude and zero frequency;
    b. displaying an axis of the polar coordinate plot representing reflected signals of the reference pulsed acoustic signal having zero frequency;
    c. displaying each color on the polar coordinate plot at a radius with respect to the origin, the radius representing amplitude information of reflected doppler display signals of the reference pulsed acoustic signal;
    d. displaying each color at an angle on the polar coordinate plot with respect to the axis, the angle representing a frequency of reflected signals of the reference pulsed acoustic signal; and
    e. displaying a vector on the polar coordinate plot displaced 180 degrees from the axis, the vector representing a Nyquist limit of the reference pulsed acoustic signal.

3. The method of claim 2 further comprising displaying colors on the polar coordinate plot in a positive direction at a point representing a maximum amplitude for first frequency towards a point representing a maximum amplitude for a second frequency ranging from a first color to a second color, colors on the plot in a negative direction from a point representing a maximum amplitude for a third frequency towards a point for a maximum amplitude for a fourth frequency ranging from a third color to a fourth color, and the colors for each frequency on the plot ranging from a color at a maximum amplitude for each frequency to a fifth color at the origin.

4. The method of claim 3 wherein the first color is red, the second color is white, the third color is blue, the fourth color is white, and the fifth color is black.

5. The method of claim 3 wherein the first frequency is zero, the second frequency is the Nyquist limit, the third frequency is zero and the fourth frequency is the Nyquist limit.

6. The method of claim 3 further comprising a user defining the first, second, third, and fourth frequencies, and the first color being displayed for all frequencies from the axis to the point representing the first frequency at a maximum amplitude in a positive direction, the second color being displayed for all frequencies from the second frequency to the Nyquist limit at a maximum amplitude in a positive direction, the third color being displayed for all frequencies from the axis to the point representing the third frequency at a maximum amplitude in a negative direction, and the second color being displayed for all frequencies from the fourth frequency to the Nyquist limit at a maximum amplitude in a negative direction.

7. The method of claim 3 wherein the first, third and fifth colors are black, and the second and fourth colors are magenta.

8. A method of displaying an image comprising reflected doppler display signals in real time produced by reflecting a reference pulsed acoustic signal, each reflected display signal being displayed in a color defined by displaying a polar coordinate plot, comprising the following steps:
    a. displaying an origin of the polar coordinate plot representing reflected signals of the reference pulsed acoustic signal having maximum variance;

b. displaying an axis on the polar coordinate plot representing reflected signals of the reference pulsed acoustic signal having zero frequency c. displaying each color on the polar coordinate plot at a radius with respect to the origin, the radius representing variance information of reflected signals of the reference pulsed acoustic signal, wherein the maximum radius on the polar coordinate plot represents reflected signals having minimum variance;

d. displaying each color on the polar coordinate plot at an angle with respect to the axis, the angle representing a frequency of reflected signals of the reference pulsed acoustic signal; and displaying a vector on the polar coordinate plot displaced 180 degrees from the axis of the polar coordinate plot, the vector representing a Nyquist limit of the reference pulsed acoustic signal.

9. The method of claim 8 further comprising using colors on the polar coordinate plot ranging from a first color for reflected signals having a maximum variance, to a second color for reflected signals having a minimum variance.

10. The method of claim 9 wherein the first color is green and the second color is black.

* * * * *